United States Patent
Schwamb

(10) Patent No.: US 11,540,845 B2
(45) Date of Patent: Jan. 3, 2023

(54) HIGH SPEED CUTTING BUR

(71) Applicant: Medtronic Xomed, Inc., Jacksonville, FL (US)

(72) Inventor: Jeffrey M. Schwamb, Broomfield, CO (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 178 days.

(21) Appl. No.: 17/076,499

(22) Filed: Oct. 21, 2020

(65) Prior Publication Data
US 2022/0117612 A1      Apr. 21, 2022

(51) Int. Cl.
*A61B 17/16* (2006.01)

(52) U.S. Cl.
CPC ...... *A61B 17/1688* (2013.01); *A61B 17/1615* (2013.01); *A61B 17/1626* (2013.01); *A61B 17/1631* (2013.01); *A61B 17/1695* (2013.01)

(58) Field of Classification Search
CPC . A61B 17/16; A61B 17/1615; A61B 17/1617; A61B 17/1622; A61B 17/1624; A61B 17/1626; A61B 17/1628; A61B 17/1631; A61B 17/1662; A61B 17/1688; A61B 17/1695; F16C 19/00; F16C 19/02; F16C 19/04; F16C 19/08
See application file for complete search history.

(56) References Cited

U.S. PATENT DOCUMENTS

| | | | | |
|---|---|---|---|---|
| 9,155,555 B2* | 10/2015 | O'Brien, II | ...... | A61B 17/32002 |
| 9,974,558 B2* | 5/2018 | O'Brien, II | ...... | A61B 17/32002 |
| 11,259,855 B2* | 3/2022 | Bowen | ............ | A61B 17/00234 |
| 2007/0100334 A1* | 5/2007 | McFarlin | ............ | A61B 17/1622 606/45 |
| 2010/0286694 A1* | 11/2010 | Rio | .................... | A61B 17/1617 606/80 |
| 2013/0197552 A1* | 8/2013 | O'Brien, II | ...... | A61B 17/32002 606/1 |
| 2014/0298659 A1* | 10/2014 | Lescorail | ................ | F16C 35/06 29/898.063 |
| 2016/0022301 A1* | 1/2016 | O'Brien, II | ...... | A61B 17/32002 606/171 |

(Continued)

FOREIGN PATENT DOCUMENTS

| | | |
|---|---|---|
| EP | 3799807 A1 | 4/2021 |
| WO | 2019049736 A1 | 3/2019 |

OTHER PUBLICATIONS

Extended European Search Report regarding Application No. 21204025.7, dated Mar. 14, 2022.

*Primary Examiner* — Eric S Gibson
(74) *Attorney, Agent, or Firm* — Carter, DeLuca & Farrell LLP

(57) ABSTRACT

A cutting bur assembly including a cutting head with a head shaft extending therefrom. The cutting head and the head shaft are rotatable by a motor. A tube with the head shaft is rotatably mounted therein. The head shaft extends out from within the tube to locate the cutting head beyond a distal end of the tube. A plurality of bearing rollers are in direct cooperation with an outer surface of the head shaft such that upon rotation of the head shaft the plurality of bearing rollers roll along the outer surface. An outer bearing race surrounds the plurality of bearing rollers and the head shaft to retain the plurality of bearing rollers in cooperation with the head shaft.

19 Claims, 2 Drawing Sheets

(56) References Cited

U.S. PATENT DOCUMENTS

| | | | |
|---|---|---|---|
| 2017/0007272 A1* | 1/2017 | Weitzman | A61B 17/1633 |
| 2019/0262006 A1* | 8/2019 | Schwamb | A61B 17/32002 |
| 2019/0262009 A1* | 8/2019 | Cheng | A61B 17/1617 |
| 2019/0374236 A1* | 12/2019 | Weitzman | A61B 17/32002 |
| 2021/0100563 A1* | 4/2021 | Sansoucy | A61B 17/1615 |
| 2021/0100564 A1* | 4/2021 | Magno | A61B 17/32002 |
| 2021/0220983 A1* | 7/2021 | Schwamb | B25F 3/00 |
| 2022/0117612 A1* | 4/2022 | Schwamb | A61B 17/1615 |
| 2022/0133336 A1* | 5/2022 | Tsai | A61B 17/162 606/80 |

* cited by examiner

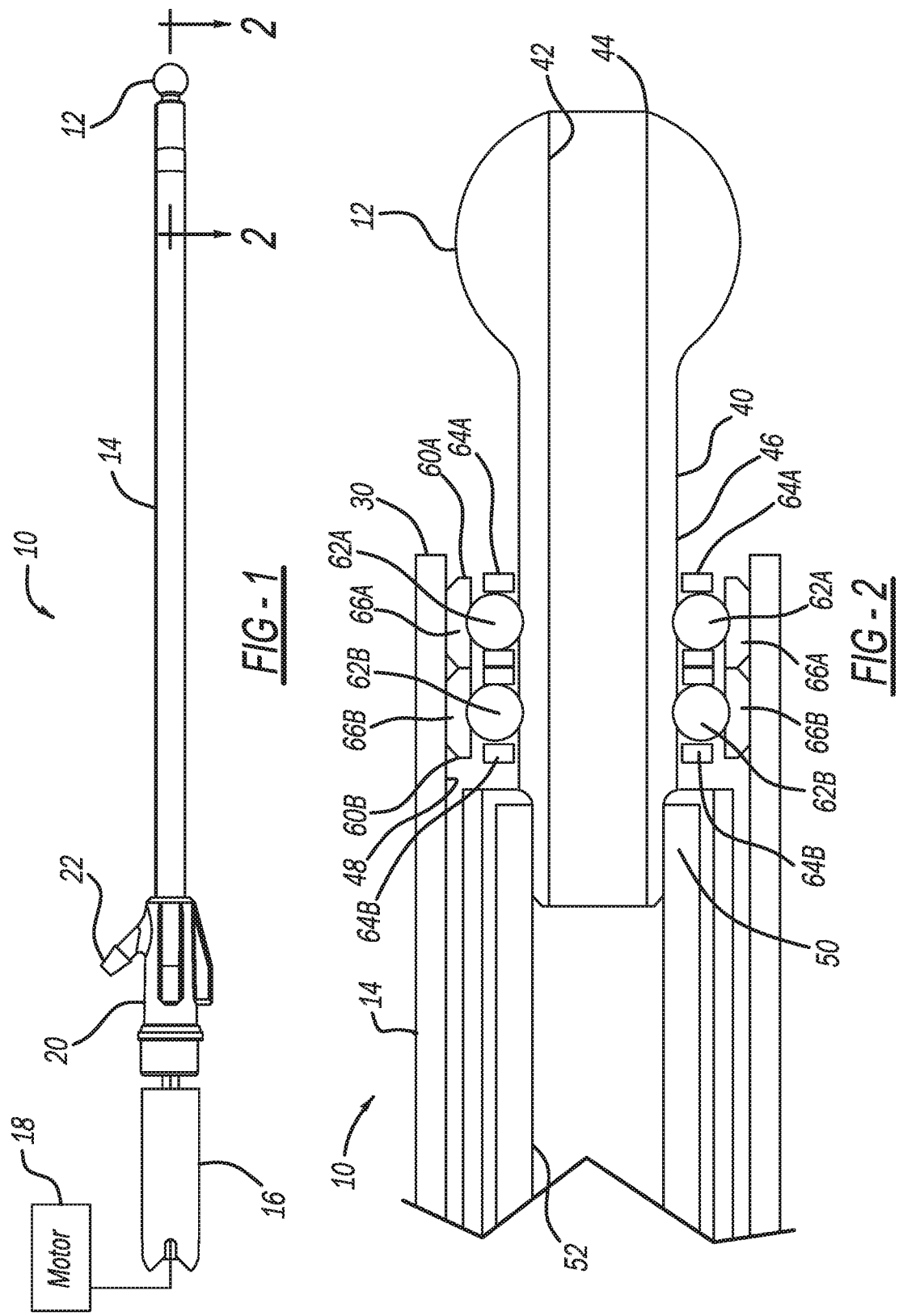

HIGH SPEED CUTTING BUR

FIELD

The present disclosure relates to a high speed cutting bur, such as for medical applications (including trans-nasal and skull-based surgery, for example), as well as non-medical applications.

BACKGROUND

This section provides background information related to the present disclosure, which is not necessarily prior art.

A cutting bur is a powered instrument including a cutting head, which is similar to a drill bit. It is desirable to operate a cutting bur at as high a speed as reasonable for the particular application in order to provide fast resection and enhanced stability of the instrument. Stability is important when operating near critical anatomy, and provides a surgeon with confidence that he/she can operate in delicate areas with maximum control. Cutting burs are often used in trans-nasal sinus and skull-based surgery, for example.

The operating speed of current cutting burs is limited, often to speeds of 30,000 RPM. At speeds greater than 30,000 RPM, current cutting burs may not operate as intended. A cutting bur configured for operating at speeds in excess of 30,000 RPM would thus be desirable. The present disclosure advantageously provides for such a high-speed bur, as described in detail herein. The present disclosure provides numerous additional advantageous and unexpected results, as described herein and as one skilled in the art will appreciate.

SUMMARY

This section provides a general summary of the disclosure, and is not a comprehensive disclosure of its full scope or all of its features.

The present disclosure includes a cutting bur assembly having a cutting head with a head shaft extending therefrom. The cutting head and the head shaft are rotatable by a motor. A tube with the head shaft is rotatably mounted therein. The head shaft extends out from within the tube to locate the cutting head beyond a distal end of the tube. A plurality of bearing rollers are in direct cooperation with an outer surface of the head shaft such that upon rotation of the head shaft the plurality of bearing rollers roll along the outer surface. An outer bearing race surrounds the plurality of bearing rollers and the head shaft to retain the plurality of bearing rollers in cooperation with the head shaft.

The present disclosure further includes a cutting bur assembly having a cutting head with a head shaft extending therefrom. The cutting head and the head shaft are rotatable by a motor. The cutting head defines an opening at a distal end of the cutting head. A head channel defined by the cutting head and the head shaft extends from the opening through the cutting head and the head shaft. A tube is rotatably mounted in the head shaft. The head shaft extends out from within the tube to locate the cutting head beyond a distal end of the tube. A first bearing includes a first inner bearing race defined by the head shaft. A first outer bearing race is in cooperation with an inner surface of the tube. A plurality of first bearing rollers are in cooperation with the first inner bearing race and the first outer bearing race. A second bearing includes a second inner bearing race defined by the head shaft spaced apart from the first inner bearing race, a second outer bearing race in cooperation with the inner surface of the tube, and a plurality of second bearing rollers in cooperation with the second inner bearing race and the second outer bearing race. The cutting head is configured to be rotated at more than about 30,000 RPM.

A method for operating a cutting bur assembly including a bur head and a bur head shaft extending therefrom. The method includes the following: connecting the cutting bur assembly to a motor configured to rotate the bur head and the bur head shaft in excess of about 30,000 RPM with the bur head shaft seated within a pair of bearings each including a plurality of bearing rollers in direct contact with an outer surface of the bur head shaft; activating the motor to rotate the bur head in excess of about 30,000 RPM; and cutting a surface with the bur head rotating in excess of about 30,000 RPM.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of select embodiments and not all possible implementations, and are not intended to limit the scope of the present disclosure.

FIG. 1 is a side view of an exemplary cutting bur assembly in accordance with the present disclosure;

FIG. 2 is a cross-sectional view taken along line 2-2 of FIG. 1;

Corresponding reference numerals indicate corresponding parts throughout the several views of the drawings.

DETAILED DESCRIPTION

Figure 3:
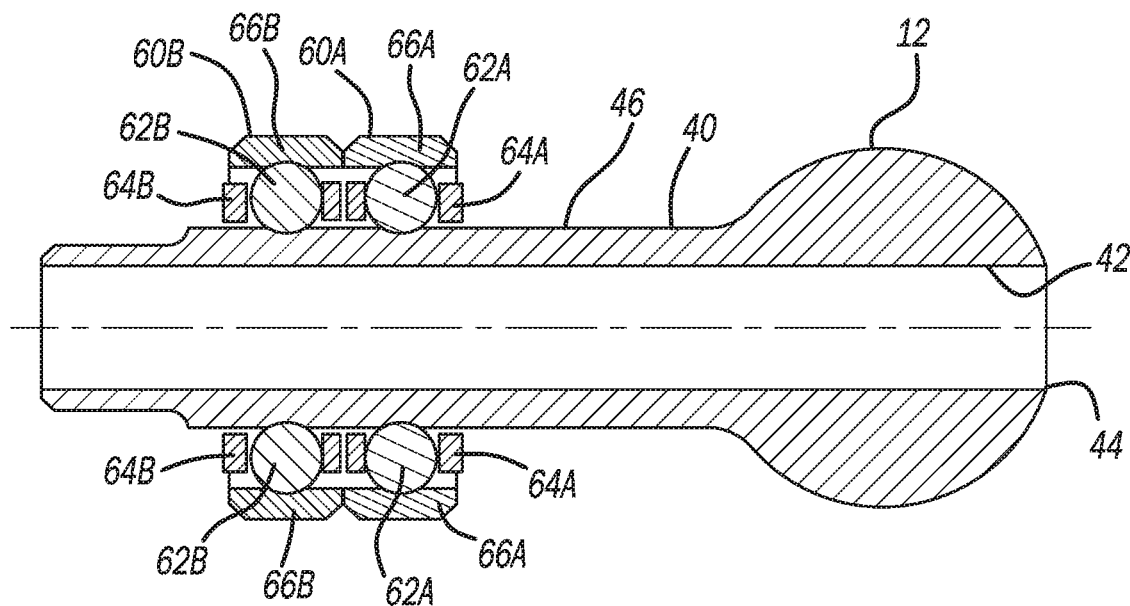
FIG. 3 is a cross-sectional view of a bur head and associated bearings of the cutting bur of FIG. 1 in accordance with the present disclosure.

Example embodiments will now be described more fully with reference to the accompanying drawings.

FIG. 1 illustrates an exemplary high speed cutting bur assembly in accordance with the present disclosure at reference numeral 10. The cutting bur assembly 10 is configured for cutting any suitable anatomic or non-anatomic surface. With respect to anatomic services, the cutting bur assembly time is configured for trans-nasal sinus or skull-based surgeries, for example. Although current cutting burs are limited to speeds of about 30,000 RPM, the cutting bur assembly 10 of the present disclosure is advantageously configured to operate at speeds higher than 30,000 RPM, such as speeds of 60,000 RPM or above. As a result, the cutting bur assembly 10 is capable of cutting surfaces, such as bone for example, with greater speed, stability, and control. The cutting bur assembly 10 provides numerous additional advantages as well, as explained herein and as one skilled in the art will appreciate.

The cutting bur assembly 10 includes a cutting head 12, which may be any suitable cutting head configured to cut and/or grind a surface of interest, such as bone or any suitable non-anatomic surface. The head 12 may include a diamond coating with any suitable cutting flute configuration. The head 12 may also be configured with any other suitable coating and geometry to facilitate cutting.

The head 12 is just beyond a distal end of an outer tube or shaft 14. The head 12 is in cooperation with an inner hub 16, which is rotated by a motor 18. Rotation of the inner hub 16 by the motor 18 rotates the head 12. The motor 18 may be any motor suitable for rotating the head 12 (by way of the inner hub 16) at speeds of 30,000 RPM or higher, such as 60,000 RPM. The motor 18 may be any suitable pneumatic motor, electric motor, etc.

The cutting bur assembly 10 further includes an outer hub 20 having an irrigation port 22. The irrigation port 22 is in fluid communication with the head 12 in any suitable manner so that a suitable irrigation fluid, such as saline, inserted through the irrigation port 22 travels to or proximate to the head 12 in order to irrigate the area being cut, grinded, etc.

With additional reference to FIG. 2, the head 12 includes a head shaft 40 extending from the head 12 into an opening in the outer tube 14 defined at a distal end 30 of the outer tube 14. A head channel 42 is defined by the head 12 and the head shaft 40. The head channel 42 extends from an opening 44 of the head 12 at a distal end of the head 12 through both the head 12 and the head shaft 40, and to the outer tube 14. The head shaft 40 extends into the outer tube 14 at the distal end 30 of the outer tube 14.

The head shaft 40 is in cooperation with an inner tube 50 extending through the outer tube 14. The inner tube 50 is in cooperation with the inner hub 16, such that rotation of the inner hub 16 by the motor 18 rotates the inner tube 50, which rotates the head shaft 40 and the head 12. The inner tube 50 defines a channel 52. The channel 52 is in fluid communication with the head channel 42. The channel 52 may be in cooperation with any suitable vacuum source for drawing debris at the cutting/grinding site through the opening 44 of the head 12, the head shaft 40, and the channel 52 to any suitable collection area.

Figure 4:
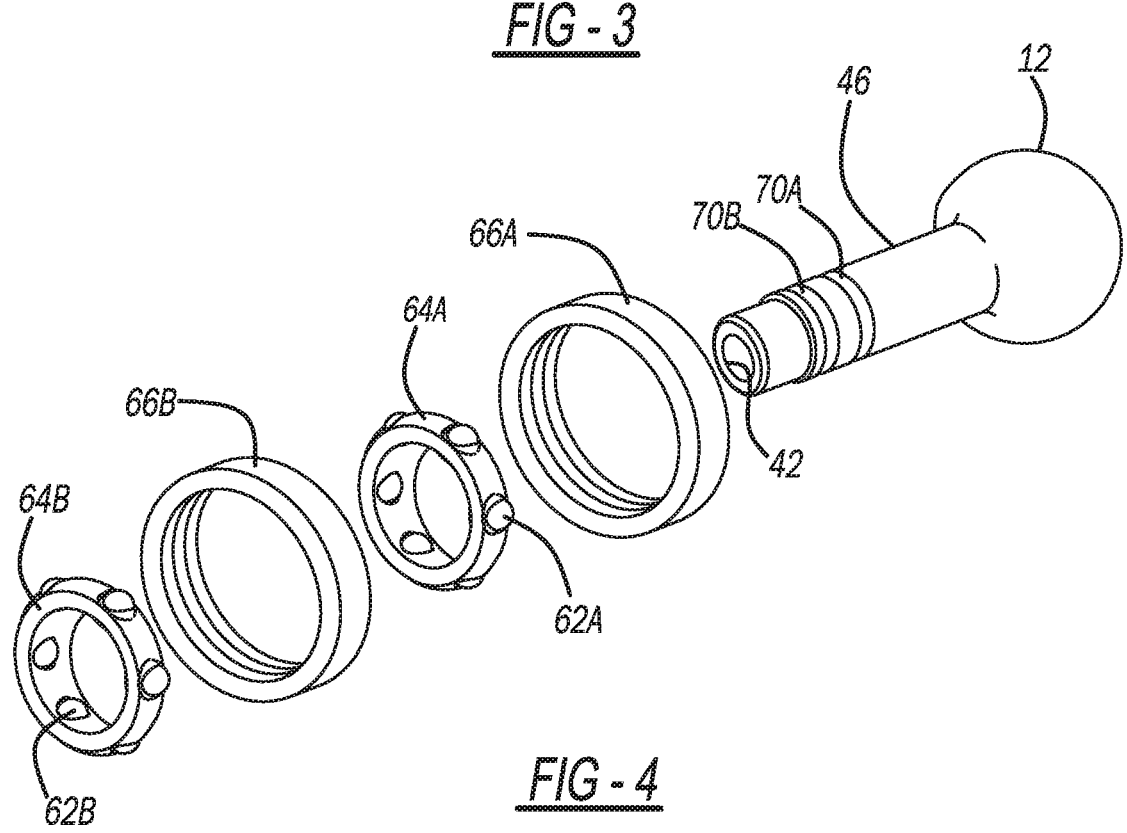
FIG. 4 is an exploded view of the bur head and associated bearings.

With continued reference to FIGS. 1 and 2, and additional reference to FIGS. 3 and 4, the head shaft 40 is mounted on one or more bearing assemblies, such as a first bearing assembly 60A and a second bearing assembly 60B. Although the cutting bur assembly 10 is illustrated as including two bearing assemblies 60A, 60B, the cutting bur assembly 10 may include only one of the bearing assemblies 60A, 60B. In other applications, the cutting bur assembly 10 may include more than two bearing assemblies configured in a manner similar to, or the same as, the bearing assemblies 60A, 60B, or configured in any other suitable manner.

The first bearing assembly 60A generally includes a plurality of first bearing rollers 62A, a first cage 64A, a first outer race 66A, and a first inner race 70A. As explained herein, the first inner race 70A (and a second inner race 70B) are both a machined outer surface 46 of the head shaft 40. The first bearing assembly 60A is arranged proximate to the distal end 30 of the outer tube 14, such as flush or nearly flush with the distal end 30. The first bearing rollers 62A may be any suitable rollers (including bearing balls) made of any suitable material, such as stainless steel. With particular reference to FIG. 4, the first bearing rollers 62A are held spaced apart by the first cage 64A such that the first bearing rollers 62A are evenly spaced apart about the first cage 64A. Any suitable number of first bearing rollers 62A may be used. The first bearing cage 64A may be made of any suitable material, such as Torlon®, for example, which is available from Solvay S.A. of Brussels, Belgium.

The first outer race 66A surrounds the first cage 64A and the bearing rollers 62A therein. The first outer race 66A is secured within the outer tube 14 in any suitable manner, such as with a press fit against an inner surface 48 of the outer tube 14. The first outer race 66A may be made of any suitable material, such as 440 series stainless steel, or any other suitable steel. The first inner race 70A, which is the machined outer surface 46 of the head shaft 40, may be made of stainless steel, such as 440 series stainless steel, or any other suitable steel.

The first inner race 70A may be a concave surface extending entirely around the outer surface 46. The first inner race 70A may be machined into the outer surface 46, or formed in any other suitable manner. As the head shaft 40 rotates, the first bearing rollers 62A advantageously roll along both the first inner race 70A and the first outer race 66A. The first bearing rollers 62A do not slide against the first inner race 70A or the first outer race 66A, which results in undesirable friction. The first and second outer races 66A, 66B remain stationary as the inner tube 50 rotates the head 12 and head shaft 40.

The second bearing assembly 60B is substantially similar to, or the same is, the first bearing assembly 60A. Thus, the description of the first bearing assembly 60A so applies to the second bearing assembly 60B. Features of the second bearing assembly 60B that are similar to, or the same as, features of the first bearing assembly 60A are designated throughout the drawings with the same reference numerals as the first bearing assembly 60A, but the suffix "A" is replaced with "B."

The second bearing assembly 60B is arranged inward of the first bearing assembly 60A. The first and second bearing assemblies 60A, 60B abut one another. Specifically, the first outer race 66A abuts the second outer race 66B, such as to help maintain the positions of the first and second bearing assemblies 60A, 60B when the cutting bur assembly 10 is operated at high speeds, such as 60,000 RPM.

The first and second bearing assemblies 60A, 60B may be pre-assembled, or preloaded, onto the head shaft 40. With the first and second bearing assemblies 60A, 60B assembled thereto, the head 12 may be easily inserted into the distal end 30 of the outer tube 14 to place the head shaft 40 into cooperation with the inner tube 50 to allow the head 12 to be driven by the motor 18, and the first and second bearing assemblies 60A, 60B may be placed in cooperation with the inner surface 48 of the outer tube 14 to hold the head 12 in a stabilized position. The head 12 may be selected from a plurality of different heads each including the first and second bearing assemblies 60A, 60B, which may be "plugged" in through the distal end 30 of the outer tube 14 for use with the cutting bur assembly 10. The head 12 may be disposable, and be replaced with another head including the first and second bearing assemblies 60A, 60B as appropriate for a particular use application.

The present disclosure thus advantageously provides for the cutting bur assembly 10 with the first and second bearing assemblies 60A, 60B, which allow the head 12 to be rotated at speeds of greater than 30,000 RPM, such as at 60,000 RPM or higher. The first and second bearing assemblies 60A, 60B advantageously do not increase the outer diameter of the outer tube 14 of existing cutting bur assemblies, thereby allowing the operator (such as a surgeon, for example) of the cutting bur assembly 10 to have a generally unobstructed view of the area being cut, grinded, etc. Providing the first and second inner races 70A, 70B as machined surfaces of the head shaft 40 advantageously helps to keep the diameter of the outer tube 14 at a diameter that is no greater than existing outer diameters. For example, the diameter of the outer tube 14 may be 4 mm, or about 4 mm. The first and second bearing assemblies 60A, 60B retain the head shaft 40 within the outer tube 14 and prevent axial displacements during high speed operation. One skilled in the art will appreciate that the present disclosure provides numerous additional advantages in addition to those specifically recited above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A cutting bur assembly comprising:
   a cutting head with a head shaft extending therefrom, the cutting head and the head shaft are rotatable by a motor;
   a tube in which the head shaft is rotatably mounted, the head shaft extends out from within the tube to locate the cutting head beyond a distal end of the tube;
   a plurality of bearing rollers in direct cooperation with an outer surface of the head shaft such that upon rotation of the head shaft the plurality of bearing rollers roll along the outer surface;
   an outer bearing race surrounding the plurality of bearing rollers and the head shaft to retain the plurality of bearing rollers in cooperation with the head shaft; and
   a cage holding the plurality of bearing rollers spaced-apart from each other.

2. The cutting bur assembly of claim 1, wherein the cutting head is configured to be rotated at more than 30,000 RPM.

3. The cutting bur assembly of claim 1, wherein the cutting head is configured to be rotated at least at 60,000 RPM.

4. The cutting bur assembly of claim 1, wherein the outer surface of the head shaft defines an annular recess in which the bearing rollers are seated.

5. The cutting bur assembly of claim 4, wherein the outer surface of the head shaft is an inner bearing race.

6. The cutting bur assembly of claim 1, wherein the cage is made of a polymeric material.

7. The cutting bur assembly of claim 1, wherein the cutting head defines an opening at a distal end of the cutting head, a head channel defined by the cutting head and the head shaft extends from the opening through the cutting head and the head shaft.

8. The cutting bur assembly of claim 1, wherein the plurality of bearing rollers are included with a first bearing assembly; and
   wherein a second bearing assembly is spaced apart from the first bearing assembly on the head shaft.

9. A cutting bur assembly comprising:
   a cutting head with a head shaft extending therefrom, the cutting head and the head shaft are rotatable by a motor, the cutting head defines an opening at a distal end of the cutting head, a head channel defined by the cutting head and the head shaft extends from the opening through the cutting head and the head shaft;

a tube in which the head shaft is rotatably mounted, the head shaft extends out from within the tube to locate the cutting head beyond a distal end of the tube;

a first bearing including a first inner bearing race defined by the head shaft, a first outer bearing race in cooperation with an inner surface of the tube, and a plurality of first bearing rollers in cooperation with the first inner bearing race and the first outer bearing race; and a second bearing including a second inner bearing race defined by the head shaft spaced apart from the first inner bearing race, a second outer bearing race in cooperation with the inner surface of the tube, and a plurality of second bearing rollers in cooperation with the second inner bearing race and the second outer bearing race;

wherein the cutting head is configured to be rotated at more than 30,000 RPM.

10. The cutting bur assembly of claim 9, wherein the cutting head is configured to be rotated at least at 60,000 RPM.

11. The cutting bur assembly of claim 9, wherein the first inner bearing race is a first annular concave surface of the head shaft and the second inner bearing race is a second annular concave surface of the head shaft.

12. The cutting bur assembly of claim 9, wherein the plurality of first bearing rollers are held spaced apart in a first cage, and the plurality of second bearing rollers are held spaced apart in a second cage.

13. The cutting bur assembly of claim 9, wherein the first outer bearing race abuts the second outer bearing race.

14. A method for operating a cutting bur assembly including a bur head and a bur head shaft extending therefrom, the method comprising:

connecting the cutting bur assembly to a motor configured to rotate the bur head and the bur head shaft in excess of 30,000 RPM with the bur head shaft seated within a pair of bearings each including a plurality of bearing rollers in direct contact with an outer surface of the bur head shaft and a first outer bearing race and a second outer bearing race;

activating the motor to rotate the bur head in excess of 30,000 RPM; and cutting a surface with the bur head rotating in excess of 30,000 RPM.

15. The method of claim 14, further comprising: activating the motor to rotate the bur head in excess of 60,000 RPM, and cutting the surface with the bur head rotating in excess of 60,000 RPM.

16. The method of claim 14, wherein the surface is a non-anatomical surface.

17. The method of claim 14, wherein the surface is an anatomical surface.

18. The method of claim 14, further comprising drawing material through a channel defined by the bur head and the bur head shaft with a vacuum during the cutting.

19. The method of claim 18, wherein the material is non-anatomical.

* * * * *